US012766019B2

(12) United States Patent
Anderson et al.

(10) Patent No.: US 12,766,019 B2
(45) Date of Patent: Oct. 20, 2026

(54) DELIVERY SYSTEM FOR DELIVERING A CARDIOVASCULAR DEVICE

(71) Applicant: Medtronic Vascular, Inc., Santa Rosa, CA (US)

(72) Inventors: April K. Anderson, Santa Rosa, CA (US); Jeremy J. Kinkade, Larkspur, CO (US); Manthan P. Patel, Santa Rosa, CA (US); Timothy K. Bertini, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 186 days.

(21) Appl. No.: 17/555,847

(22) Filed: Dec. 20, 2021

(65) Prior Publication Data

US 2023/0190502 A1 Jun. 22, 2023

(51) Int. Cl.
*A61F 2/966* (2013.01)
*A61F 2/07* (2013.01)

(52) U.S. Cl.
CPC ................ *A61F 2/966* (2013.01); *A61F 2/07* (2013.01); *A61F 2002/9665* (2013.01); *A61F 2250/0098* (2013.01)

(58) Field of Classification Search
CPC .... A61F 2/966; A61F 2/07; A61F 2002/9665; A61F 2250/0098; A61F 2002/9505;
(Continued)

(56) References Cited

U.S. PATENT DOCUMENTS 5,709,703 A * 1/1998 Lukic ........................ A61F 2/95 606/198
6,245,100 B1 * 6/2001 Davila ...................... A61F 2/91 606/198

(Continued)

FOREIGN PATENT DOCUMENTS

EP 2545887 A1 1/2013
EP 2651335 A1 10/2013

(Continued)

OTHER PUBLICATIONS

English translation of JP-2019088890 (Year: 2019).*
Extended European Search Report in European Application No. 22214696.1, mailed May 2, 2023, 9 pages.

*Primary Examiner* — Dianne Dornbusch
(74) *Attorney, Agent, or Firm* — Brooks Kushman P.C.

(57) ABSTRACT

An endovascular delivery system for delivering a stent graft within a blood vessel. The delivery system includes a guide member configured to carry the stent graft into the blood vessel and a graft cover configured to cover at least a portion of the stent graft as the guide member is inserted into the blood vessel. The stent graft including a first end and a second end, the first end closer to a proximal end of the endovascular delivery system than the second end. The guide member includes a body having an elongated shape and a non-uniform outer periphery. The non-uniform outer periphery is configured to secure a first end of the stem graft in a first position, relative to a deployment location thin the blood vessel, to hold the first end of the stent graft in the first position as the graft cover is retracted to deploy the stent graft.

20 Claims, 9 Drawing Sheets

(58) Field of Classification Search
CPC .............. A61F 2250/0019; A61F 2/962; A61F 2/2427; A61F 2/2436; A61F 2/9522; A61F 2250/0039; A61F 2/95; A61M 25/0009; A61M 25/0052; A61M 25/0108; A61M 25/0152; A61M 2025/0024; A61M 2025/0039; A61M 2025/0175
See application file for complete search history.

(56) References Cited

U.S. PATENT DOCUMENTS

| | | | | |
|---|---|---|---|---|
| 6,334,871 | B1 * | 1/2002 | Dor | A61F 2/915 623/1.34 |
| 6,520,984 | B1 * | 2/2003 | Garrison | A61F 2/915 623/1.11 |
| 7,303,580 | B2 * | 12/2007 | Parker | A61F 2/915 623/1.11 |
| 7,717,949 | B2 * | 5/2010 | Dorn | A61F 2/91 623/1.11 |
| 9,044,351 | B2 * | 6/2015 | Wang | A61F 2/91 |
| 9,180,004 | B2 * | 11/2015 | Alkhatib | A61F 2/2439 |
| 9,364,314 | B2 | 6/2016 | Berra et al. | |
| 9,375,336 | B1 | 6/2016 | Longo et al. | |
| 9,855,160 | B2 * | 1/2018 | Armstrong | A61F 2/966 |
| 10,758,350 | B2 | 9/2020 | Vaughan et al. | |
| 10,980,634 | B2 * | 4/2021 | Gallagher | A61F 2/2436 |
| 2003/0028240 | A1 * | 2/2003 | Nolting | A61F 2/07 623/1.13 |
| 2004/0059407 | A1 * | 3/2004 | Escamilla | A61B 17/1214 623/1.36 |
| 2004/0204749 | A1 * | 10/2004 | Gunderson | A61F 2/91 623/1.12 |
| 2004/0267348 | A1 * | 12/2004 | Gunderson | A61F 2/91 623/1.12 |
| 2006/0004433 | A1 * | 1/2006 | Greenberg | A61F 2/95 623/1.11 |
| 2006/0276872 | A1 * | 12/2006 | Arbefeuille | A61F 2/89 623/1.11 |
| 2008/0114443 | A1 * | 5/2008 | Mitchell | A61F 2/95 623/1.13 |
| 2008/0188804 | A1 * | 8/2008 | Jordan | A61F 2/95 604/103.04 |
| 2009/0264820 | A1 * | 10/2009 | Kung | A61F 2/2433 604/99.04 |
| 2009/0276027 | A1 * | 11/2009 | Glynn | A61F 2/95 623/1.13 |
| 2010/0030318 | A1 * | 2/2010 | Berra | A61F 2/07 623/1.11 |
| 2011/0251665 | A1 * | 10/2011 | Schmitt | A61F 2/966 623/1.11 |
| 2012/0035705 | A1 * | 2/2012 | Giasolli | A61F 2/89 623/1.11 |
| 2012/0330401 | A1 * | 12/2012 | Sugimoto | A61F 2/915 623/1.12 |
| 2013/0274859 | A1 * | 10/2013 | Argentine | A61F 2/95 623/1.11 |
| 2013/0289698 | A1 * | 10/2013 | Wang | A61F 2/2418 623/1.12 |
| 2014/0277340 | A1 * | 9/2014 | White | A61F 2/89 623/1.11 |
| 2016/0262884 | A1 * | 9/2016 | Lombardi | A61F 2/2412 |
| 2017/0281382 | A1 * | 10/2017 | Lostetter | A61F 2/07 |
| 2017/0348101 | A1 * | 12/2017 | Vaughn | A61F 2/2436 |
| 2019/0008667 | A1 * | 1/2019 | Longo | A61F 2/966 |
| 2020/0060850 | A1 * | 2/2020 | Huang | A61F 2/915 |

FOREIGN PATENT DOCUMENTS

| | | | | | |
|---|---|---|---|---|---|
| JP | 2019088890 | A | * | 6/2019 | A61F 2/07 |
| WO | 2012/061526 | A2 | | 5/2012 | |
| WO | 2013/188132 | A1 | | 12/2013 | |
| WO | 2020153249 | A1 | | 7/2020 | |

* cited by examiner

DELIVERY SYSTEM FOR DELIVERING A CARDIOVASCULAR DEVICE

TECHNICAL FIELD

The present disclosure relates generally to a delivery system for delivering a cardiovascular and a method for delivering a cardiovascular device, such as an endovascular graft within a blood vessel (e.g., the aorta).

BACKGROUND

Endovascular procedures are minimally invasive techniques to deliver a variety of clinical treatments in a patient's vasculature. One such clinical treatment that can be delivered through an endovascular procedure is a stent graft, while another is a transcatheter heart valve. A stent graft is an implantable device formed of a surgical graft and an expanding or self-expanding metal frame. The stent graft may be placed inside a blood vessel (e.g., the aorta) to bridge a diseased segment (e.g., an aneurismal segment or a dissected segment) of the blood vessel, thereby excluding or mitigating hemodynamic pressures of blood floss from the diseased segment of the blood vessel.

Endovascular grafts (e.g., stent grafts) may be deployed through, a minimally invasive intraluminal delivery procedure. A lumen or vasculature may be accessed at a convenient and less traumatic entry point of the patient's body, and the endovascular graft may be routed through the vasculature to the site where the prosthesis is to be deployed. Intraluminal deployment typically uses a delivery catheter with tubes or shafts arranged for relative axial movement. For instance, an expandable stent graft may be compressed and disposed within a distal end of an outer shaft of the delivery catheter fixed to an inner shaft. The delivery catheter may then be maneuvered, typically tracked through a body lumen until a distal end of the delivery catheter and the stem graft are positioned at an intended treatment site. The expandable stent graft can then be deployed and radially expanded within the blood vessel.

SUMMARY

According to one embodiment, an endovascular delivery system for delivering a stent graft within a blood vessel is provided. The delivery system, may include a guide member that may be configured to carry the stent graft into the blood vessel and a graft cover configured to cover at least a portion of the stent graft as the guide member is inserted into the blood vessel. The stent graft may include a first end and a second end, the first end may be arranged closer to a proximal end of the endovascular delivery system than the second end. The guide member may include a body having an elongated shape and a non-uniform outer periphery. The non-uniform outer periphery may be configured to secure a first end of the stent graft in a first portion, relative to a deployment location within the blood vessel, to hold the first end of the stent graft in the first position as the graft cover is retracted to deploy the stent graft.

According to another embodiment, an endovascular delivery system for delivering a stent graft within a blood vessel is provided. The delivery system may include a guide member and a graft cover. The graft cover may be configured to radially cover at least a portion of the stent graft and may be configured to uncover the stent graft so that the stent graft changes from a radially compressed configuration to a radially deployed configuration. The guide member may be configured to carry the stent graft and the graft cover into the blood vessel. The stent graft may include a first end portion and a second end portion, the first end portion may be positioned closer to a proximal end of the delivery system than the second end portion. The guide member may include a retaining member configured to engage and secure an end portion of the stem graft with respect to a deployment location within the blood vessel as the stent graft changes from the radially compressed configuration to the radially deployed configuration.

According to yet another embodiment, a method for delivering a stent graft within a blood vessel is provided. The method may include a positioning step, a retracting step, and holding step. The positioning step may include positioning a delivery system with a guide member configured to radially support and carry the stent graft in a radially compressed configuration at a first deployment location, so that a first end portion of the stent graft is positioned at a second deployment location. The second deployment location may be remote from the first deployment location and, a second end portion of the stem graft may be positioned closer to a proximal end of the delivery system than the first end portion of the stent graft. The retracting step may include retracting a graft cover from the stent graft so that the stent graft changes form a radially compressed configuration to the radially deployed configuration. The holding step may include holding, by a retention member of the guide member, a second end portion of the stent graft in the first deployment location.

DETAILED DESCRIPTION

Figure 1:
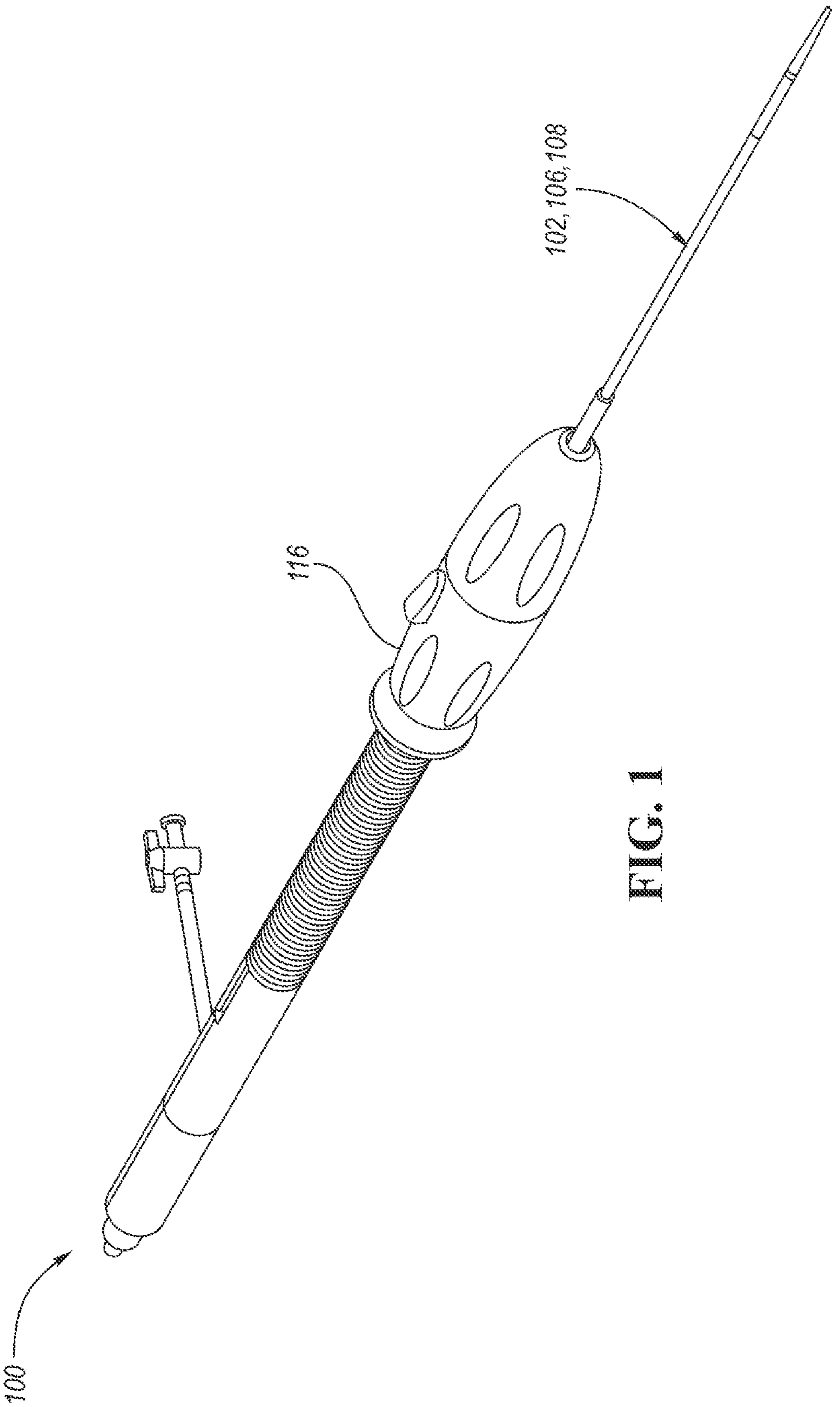
FIG. 1 illustrates a perspective view of an exemplary delivery system for delivering endovascular stent grafts.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces, faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path. For a transcatheter heart valve, "proximal" is upstream by way of blood flow path while "distal" is downstream by way of blood flow path.

The following detailed description is merely exemplary in nature and is not intended to limit the invention or the application and uses of the invention. Although the description is in the context of treatment of blood vessels such as the aorta, coronary, carotid, and renal arteries, the invention may also be used in any other body passageways where it is deemed useful.

Endovascular stent grafting, or endovascular aneurysm repair (EVAR), is a form of treatment for abdominal or thoracic aortic aneurysm that is less invasive than open surgery. Similarly, transcatheter heart valve repair or replacement (e.g., TAVR) is a form of treatment for diseased or dysfunctional heart valves that is less invasive than open surgery. Endovascular stent grafting uses an endovascular stent graft to reinforce the wall of the aorta and to help keep the damaged area from rupturing by isolating the aneurysm from blood flow. Stent grafts are typically tubular open-ended structures providing support for damaged, collapsing, or occluded blood vessels, such as the aorta. Stem grafts are flexible, which allows them to be inserted through, and conform to, tortuous pathways in the blood vessels, a process commonly referred to as "tracking." For example, stent grafts may be radially expandable from a radially compressed configuration for tracking to the affected vessel site to a radially expanded configuration when deployed at the affected vessel treatment site, commonly referred to as "deployment." The radially expanded configuration has a larger diameter than the radially compressed configuration. During deployment, stent grafts may be expanded to the radially expanded configuration either through a self-expanding mechanism, or using a balloon catheter, for example.

Stent grafts come in different forms such as main stent grafts, fenestrated stent grafts, and branched stent grafts.

Fenestrated and branched stent-grafts allow incorporation of aortic side branches and preservation of end organ perfusion. Branched stent grafts include one or more arms extending from the main stent graft that are configured to provide blood perfusion to one or more vessels extending from the aorta to the great vessels (BCA, LCC, and LSA), kidneys, or other branch vessels, via one or more branch/bridging stent grafts. Branched stent grafts may be deployed in a manner similar to the main stent graft described above.

In one example, an EVAR procedure may include inserting a guide wire into a portion of the patient's body, such as the femoral artery. Once the guidewire is inserted into the artery, it may be gently pushed toward the site of the aneurysm. A stem graft delivery system, which may include a catheter, a graft cover, stent graft and guide member, may be placed over the guidewire, and inserted along the guidewire into the site of the aneurysm. The stent graft may be guided by the guide member within the catheter in its radially compressed configuration to the site of the aneurysm. The guide member is configured to radially support the stent graft and the graft cover to prevent the graft cover from kinking during tracking.

Radiopaque (RO) markers may be located at an end portion of the stent graft delivery system or on the stent graft itself to permit a surgical technician to guide the stent graft into a proper position. Once in the proper position, the stent graft can be expanded from the radially compressed configuration to the radially expanded configuration. This can be done, for example, by pulling back a stent-graft cover, allowing the stent graft to expand due to its stent(s) being biased outwards. Once deployed, into the radially expanded configuration, the stent graft can be held in place with metallic hooks or stents (e.g., by radially outward force). The guide member may serve as a stem stop during deployment by securing a portion of the stent graft to prevent the stent graft from retracting as the graft cover is retracted.

Under certain conditions, portions of the stent graft, such as the final segment of the stent graft may lurch in an axial direction out of the graft cover as deployment nears completion, potentially affecting deployment accuracy of the stent graft. As described herein, the final segment of the stent graft is the last to be deployed as the graft cover is retracted (e.g., the end of the stent graft opposite the distal tip of the delivery system, and closer to the handle). In certain embodiments, the final segment will be the proximal segment, for example, when the final segment is closest to the heart when deployed. However, depending on the deployment approach, the final segment may be the distal segment once the stent graft is delivered.

Referring generally to the figures, a delivery system 100 for delivering a stent graft or stent graft 102 within a blood vessel 104 is provided. The stent graft 102 may be configured to change between a radially compressed configuration and a radially deployed configuration. During tracking of the stent graft 102, the stent graft 102 may be in the radially compressed configuration and during deployment, the stent graft 102 may be in the radially deployed configuration. A graft cover 106 may radially cover and compress the stent graft 102 as the stem graft 102 tracks through the blood vessel 104 to a deployment location. The graft cover 106 may be retracted to uncover the stent graft 102 so that the stent graft 102 radially expands to the radially deployed configuration.

A guide member 108, also called a middle member, may guide and carry the stent graft 102 through the blood vessel 104 so that the graft cover 106 does not kink or bend in an unintended manner. The guide member 108 may include a retaining member 110 that may be configured to engage and secure a proximal portion 103 of the stent graft with respect to the deployment location, to inhibit undesired movement, e.g., axial movement of the stent graft 102 with respect to the deployment location. As an example, the proximal portion 103 of the stent graft 102 may include an engagement member 107 that may be formed by portions of the stent graft 102 including but not limited to, a stent ring 105 (e.g., a sinusoidal or zigzag patterned ring), or stent graft wall 109, or radio opaque markers 156 that may be disposed on the proximal portion 103 of the stent graft 102.

The guide member 108 may include a main body 112 and a distal end portion 114 that may extend from a side of the main body 112 that is distal from a handle 116 of the delivery system 100. In one or more embodiments, the distal end portion 114 may include a non-uniform outer periphery that may form the retaining member 110. As an example, the distal end portion 114 may include a proximal member 118, a distal member 120, and a medial member 122 that may extend between the distal member 120 and the proximal member 118. The medial member 122 may be sized with respect to the proximal member 118 and distal member 120 to form a groove or a notch 124 that may be configured to engage and secure one or more portions of the stent graft 102 during tracking and deployment of the stent graft 102.

FIG. 1 shows a delivery system 100 according to one or more embodiments. The delivery system may include the handle 116 and the guide member 108, the stent graft 102, and the graft cover 106 may extend from the handle 116. The graft cover 106 radially covers the guide member 108 and the stent graft 102. A tapered tip may be disposed at a distal end of the graft cover 106. The delivery system 100 is just one example and the guide member 108 may be used in other delivery systems.

Figure 2:
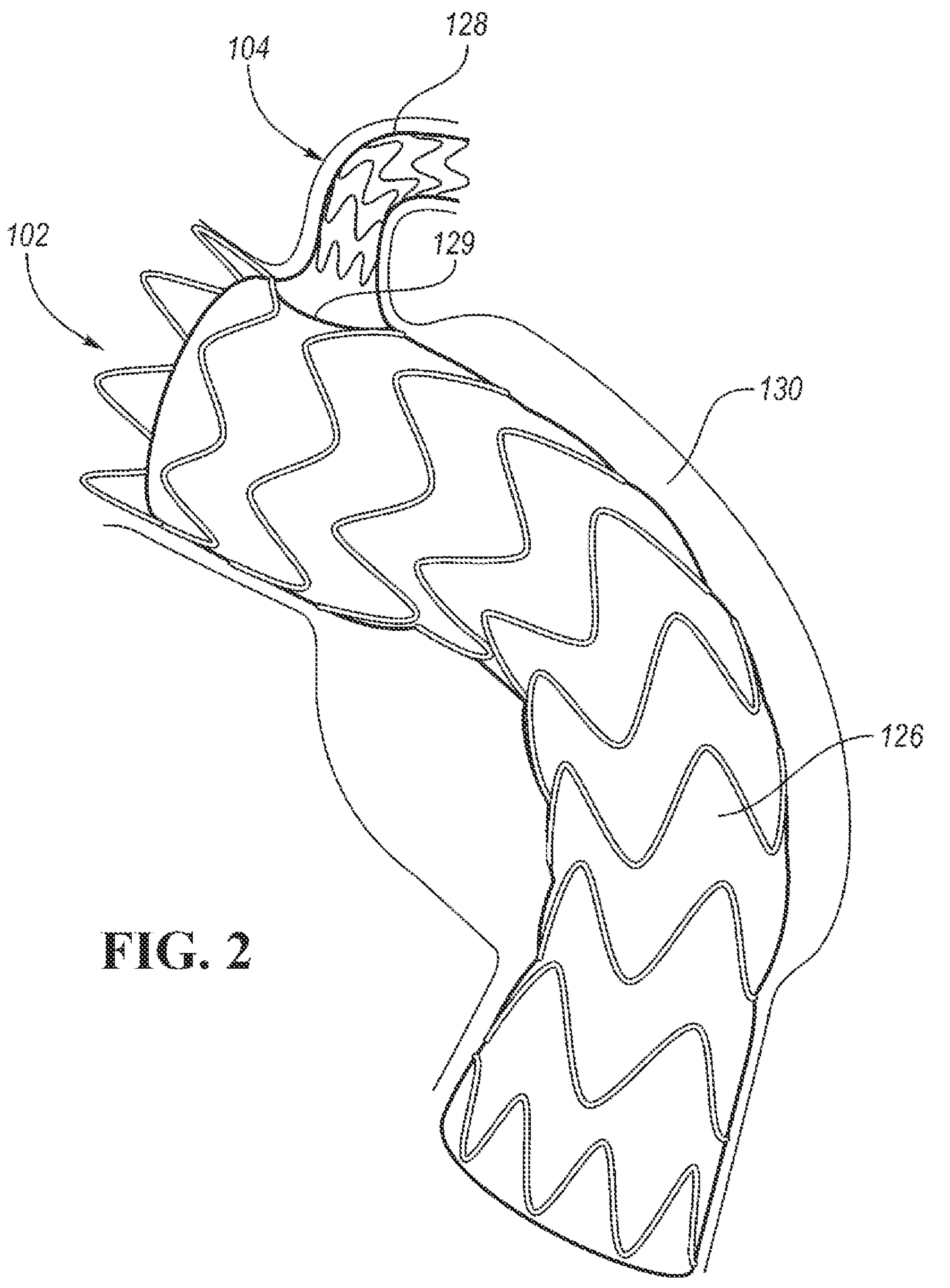
FIG. 2 illustrates an exemplary endovascular stem graft.

FIG. 2 illustrates the exemplary stent graft 102 within the blood vessel 104, the stent graft 102 may be a multi-branched stent graft, though the delivery system may be configured for use with other stent grafts including but not limited to fenestrated or iliac branch stent grafts. The stent graft may include a main stent graft 126 and a number of branch stent grafts 128 that may extend from the main stent graft 126 at opening 129. Once affixed within blood vessel 104, stent graft 102 is configured to provide a conduit for blood flow through stent graft 102. As shown in FIG. 2, the stent graft 102 is located within an aneurysm 130 of blood vessel 104. Blood flowing through the main stent graft 126 and the branch stent graft 128 of the stent graft 102 may reduce pressure within aneurysm 130 and provide blood flow to kidneys or other portions of the body, thereby reducing or stabilizing the size of aneurysm 130. Graft material of stent graft 102 may be a non-permeable material, such as polyester terephthalate (PET), expanded polyester terephthalate (ePET), polytetrafluoroethylene (PTFE), polyurethane, or silicone. Blood or other fluid is prevented from passing through the non-permeable graft material. The graft material may also be formed of a natural material such as pericardium or another membranous tissue such as intestinal submucosa. The stent of stent graft 102 may be formed of a radially compressible and expandable material configured to self-expand into apposition with the interior wall of blood vessel 104. The stent may be coupled to the graft material to support the graft material. The stent may be constructed of Nitinol, stainless steel, a pseudo-elastic metal such as a nickel titanium alloy or nitinol, various polymers, or a super alloy having a base metal of nickel, cobalt, chromium, or other metal. The stent may be formed of a stent patterned ring 105 including a number of crowns or bends and a number of struts or straight segments with crowns being formed between pairs of opposing struts.

Figure 3:
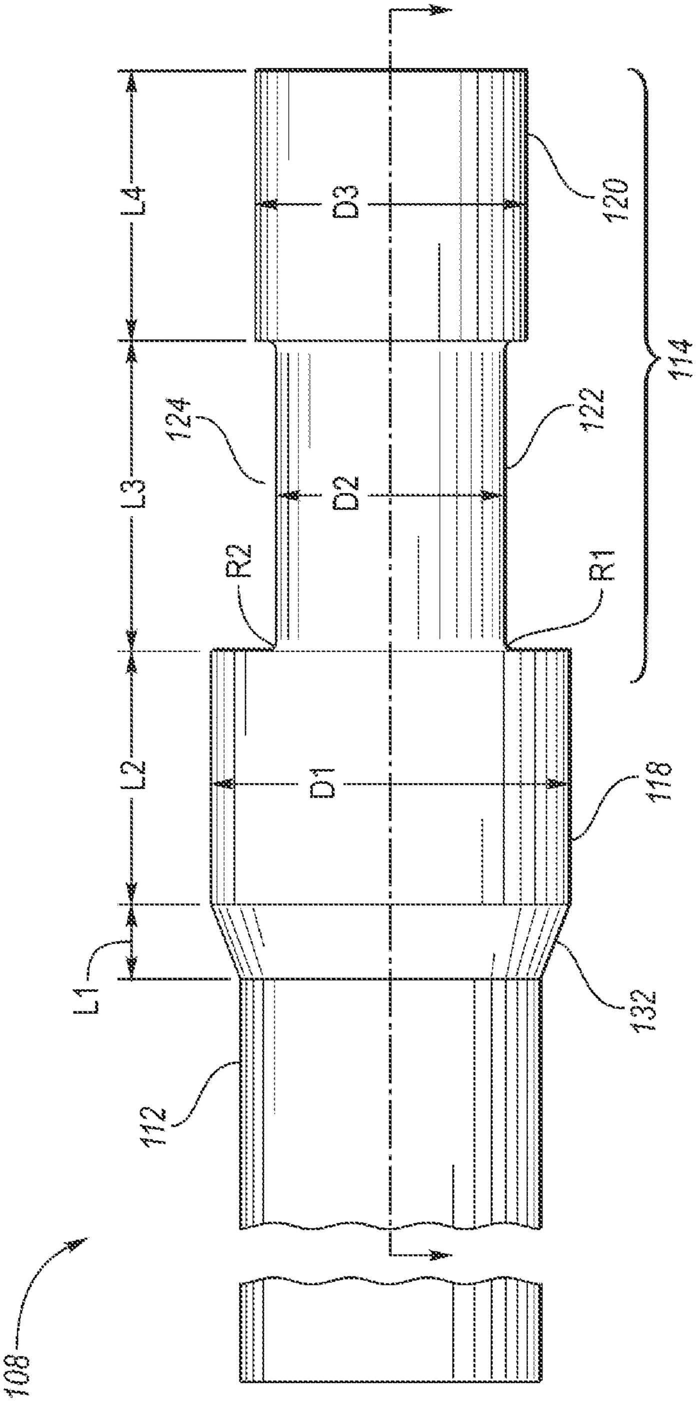
FIG. 3 illustrates a plan view of an exemplary guide member of the exemplary delivery system illustrated in FIG. 1.

FIG. 3 illustrates a plan view of the guide member 108 according to one or more embodiments. The guide member 108 may include the main body 112 and the distal end portion 114 may extend from the main body 112. The distal end member 114 may include the proximal member 118 that may be connected, to main body 112 by a flared member 132. As an example, the flared member 132 may be tapered from the proximal member 118 to the main body 112 and define a first angle α that may range between 5 degrees and 45 degrees. The distal end portion 114 may have non-uniform outer periphery or shape that may form one or portions of the retaining member 110. In one or more embodiments, the distal end portion 114, or more specifically, the proximal member 118 may have an outer diameter D1 that may be different than the outer diameter D2 of the medial member 122, and the outer diameter D3 of the distal member 120. The first outer diameter D1 of the proximal member 118 may be larger than the second outer diameter D2, and the third outer diameter D3 of the distal member 120. The third outer diameter D3 may be larger than the second outer diameter D2 of the medial member 122 and the third outer diameter D3 may be less than the first diameter D1 of the proximal member. The third outer diameter D3 of the distal member 120 may be sized to provide sufficient pack density of the stent graft 102 when the stent graft 102 is in the radially compressed configuration, while limiting the insertion forces required during tracking.

As an example, the first diameter D1 may range between 0.110 inches and 0.180 inches, the second diameter D2 of the medial member 122 may range between 0.065 inches and 0.125 inches, and the third diameter D3 of the distal member 120 may range between 0.082 inches and 0.142 inches, One or more radii R1, R2, may be formed between the proximal member 118 and the medial member 122. The radii R1, R2 may each have a radius that is less than or equal to 0.008 inches. The flared member 132 may have a first length L1 that may be greater than or equal to 0.025 inches and the proximal member 118 may be greater than the first length L1 and have a second length L2 that may be greater than or equal to 0.07 inches. The medial member 122 may have a third length L3 that may be greater than the second length L2 and may range between 0.121 inches and 0.200 inches (e.g., 3 to 5 mm). In another embodiment, the third length L3 may be about 0.161 inches (e.g., about 4 mm). The distal member 120 may have a fourth length L4 that may be less than the third length L3 and may range between 0.122 inches and 0.169 inches. Alternatively or additionally, the medial member 122 and the distal member 120 may collectively have a length that is substantially equal 0.300 inches. The above-mentioned lengths L1 to L4 are just an example and are not intended to be limiting, the guide member 108 may be sized to accommodate stent grafts 102 for loaded stent graft variation. As an example, the guide member may be formed, for example, by injection molding and trimmed to the required length.

Figure 3A:
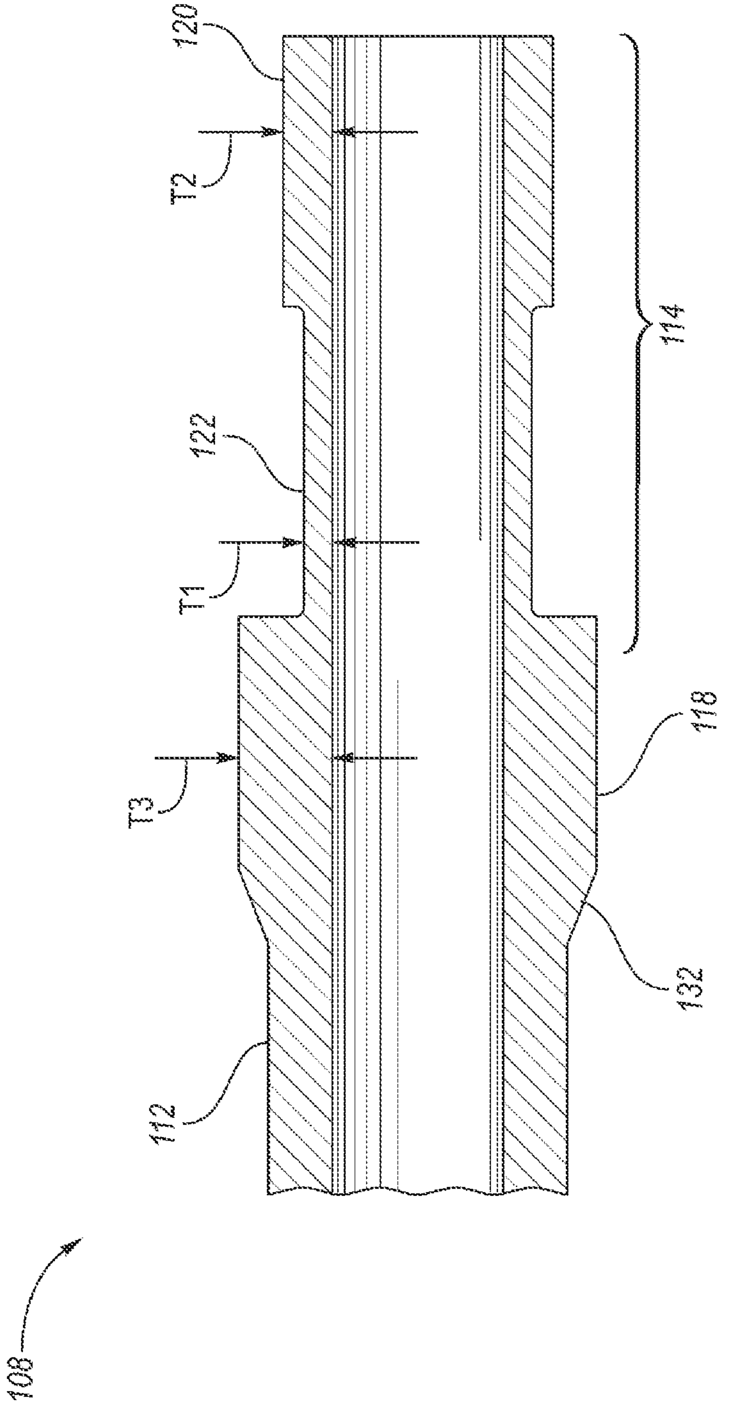
FIG. 3A illustrates a cross-sectional view of the guide n ember taken along the lines A-A in FIG. 3.

FIG. 3A illustrates a cross-sectional view of the guide member 108 taken along the lines A-A in FIG. 3. The guide member 108 may be hollow and form an aperture such as a through-opening 134 that may be substantially constant in diameter from the main body 112 through the distal end portion 114. The through-opening 134 may have an inner diameter D4 that may range between 0.058 inches and 0.088 inches. The inner diameter D4 of the through-opening 134 may be sized to receive a lumen 138 and a guide wire (not illustrated) that may be disposed in a guidewire lumen 138

Figure 6:
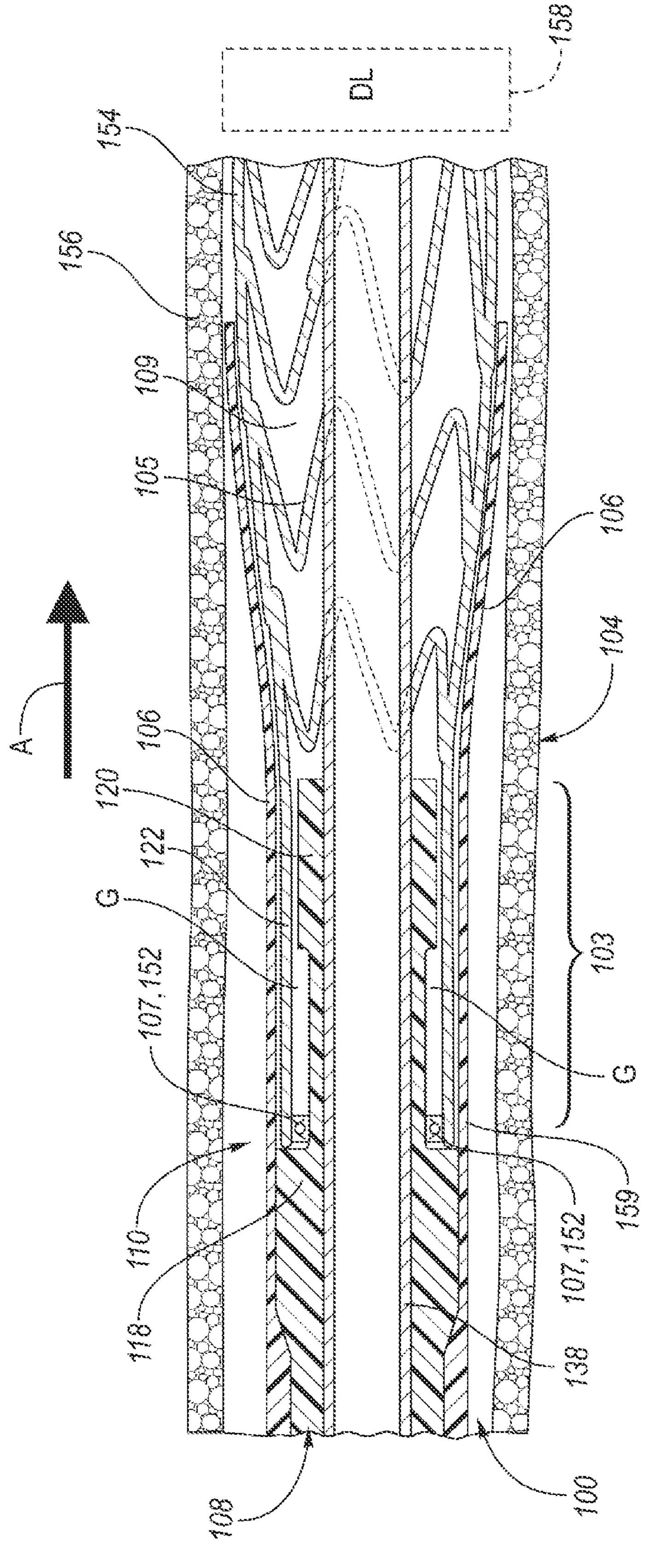
FIG. 6 illustrates cross-sectional view of the guide member shown in FIG. 3 and an exemplary stem graft during deployment the exemplary stent graft.

(FIG. 6). As another example, the through-hole 134 may receive a spindle tube (not illustrated) that may be used for bifurcated and aortic cuff delivery system. The spindle tube may receive the guidewire lumen 138. The distal end portion 114 may have a wall thickness that may vary between the proximal member 118 and the distal member 120. For example, the medial member 122 may have a first thickness T1 that may be less than a second thickness T2 of the distal member 120 and the first thickness may be greater than or equal to 0.004 inches or another thickness as required.

Figure 3B:
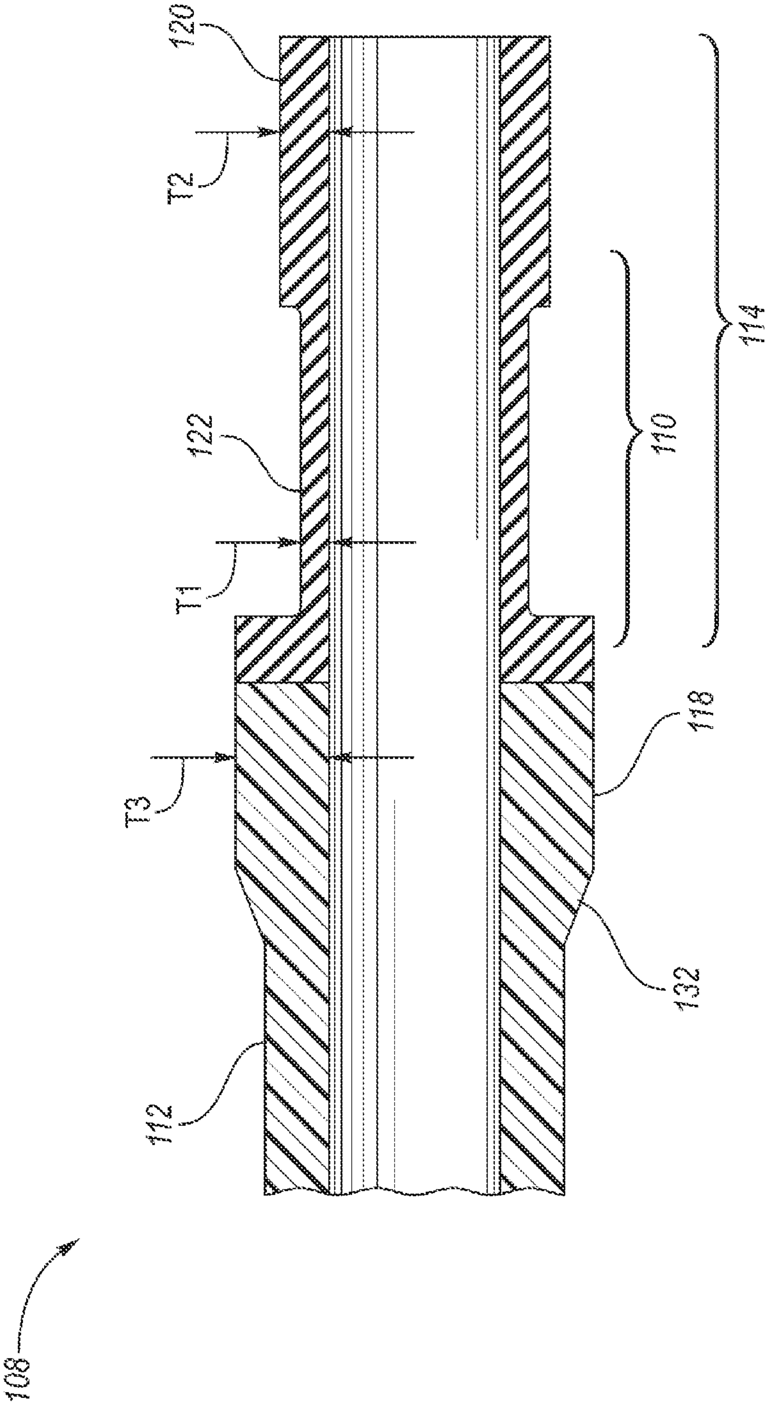
FIG. 3B illustrates a cross-sectional view of another guide member taken along the lines A-A in FIG. 3.

FIG. 3B illustrates a cross-sectional view of an over-molded guide member 136. As an example, the main body 112 may be formed of a polymeric material by injection molding and the distal end portion 114 may be formed of the same material as the main body 112 or another material over-molded to the proximal member 118. The proximal member 118 may be connected to the medial member 122 by a chemical or mechanical bond through a 2-shot molding process or an over molding process. Using an over molding or 2-shot molding process may facilitate retrofitting of guide members not provided with a distal end portion 114 and retaining member 110 with configuration illustrated in the figures and described herein. As another example, an over molding or 2-shot molding process may be suitable to form the distal end portion 114 with a softer or more elastic material than the material of the main body 112.

Figure 4:
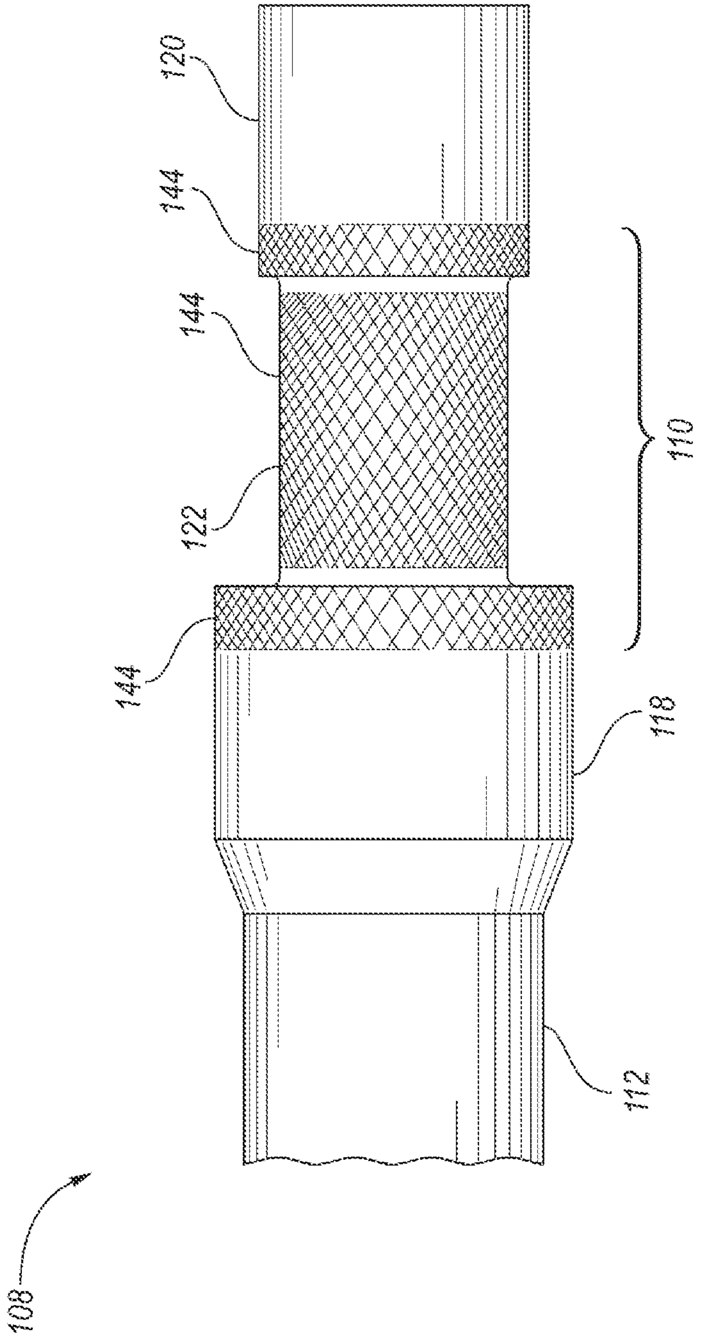
FIG. 4 illustrates a plan view of another exemplary guide member of the exemplary delivery system illustrated in FIG. 1.
Figure 7:
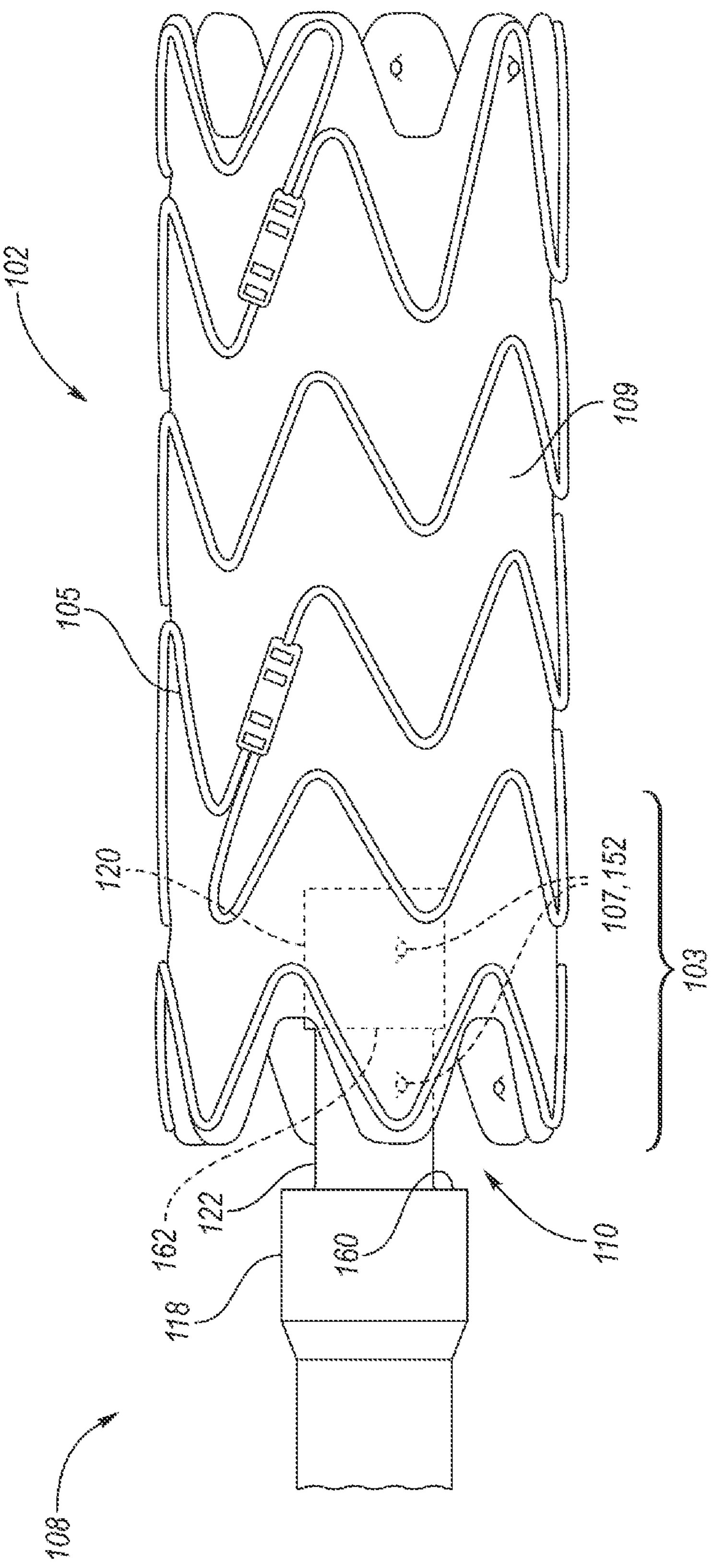
FIG. 7 illustrates a partial plan view of the guide member shown in FIG. 3 and the exemplary stem graft in a radially deployed configuration.

FIG. 4 illustrates another guide member 142 according to one or more embodiments. As an example, the retaining member 110 may be formed by one or more portions of the distal end portion 114 that may include a number of knurls 144 that may be formed on portions of the proximal member 118, distal member 120, and the medial member 122. The number of knurls 144 may be formed of a pattern of straight and crossed lines that may be rolled into the material. As another example, the number of knurls 144 may be formed during as the distal end portion 114, the guide member 142, or both is formed. The number of knurls 144 may frictionally engage the engagement member 107 that may be disposed on the proximal end 103 of the stent graft 102 (FIGS. 6 and 7). The number of knurls 144 may be disposed only on one portion of the distal end portion 114 or other portions of the distal end member 114.

Figure 5:
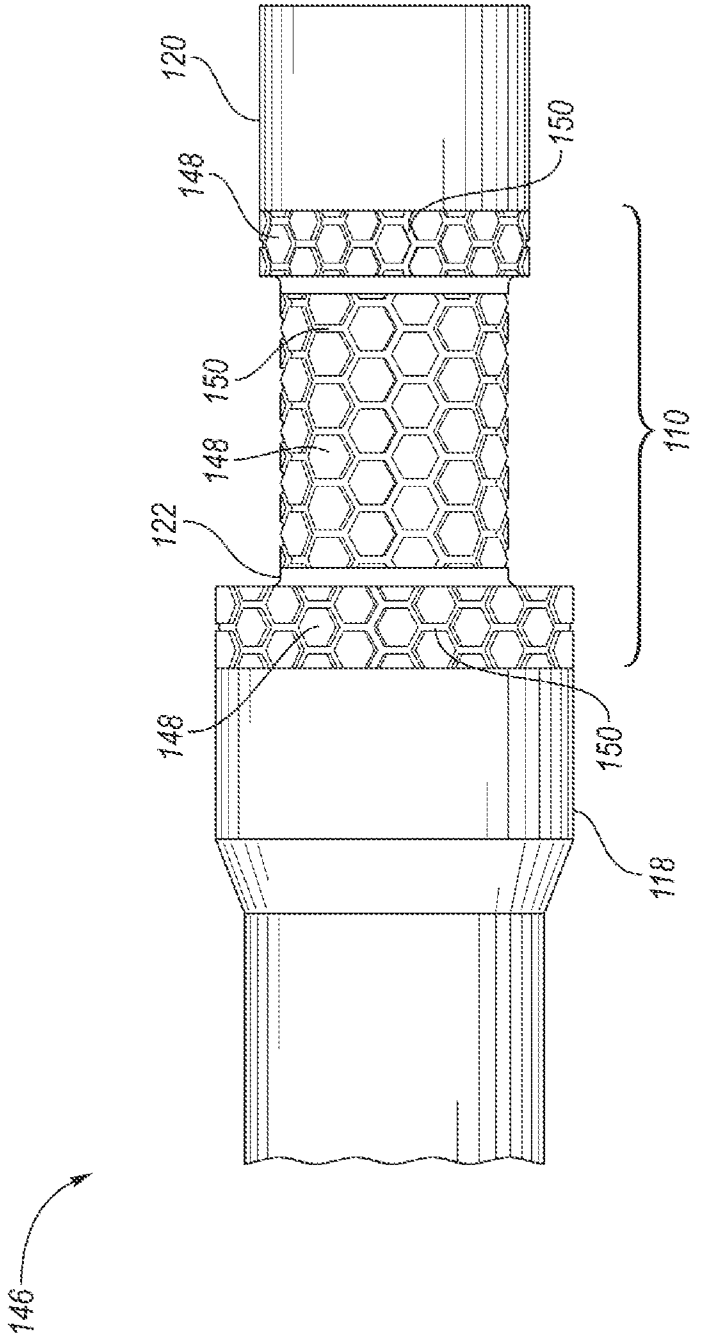
FIG. 5 illustrates a plan view of yet another exemplary guide member of the exemplary delivery system illustrated in FIG. 1.

FIG. 5 illustrates yet another guide member 146 provided with a number of protrusions 148 that may define a number of channels or interstices 150 that may be disposed between each of the protrusions 148. As an example, the protrusions 148 and the number of interstices 150 may be disposed on one or more portions of the distal end member 114 of the guide member 146 including but not limited to the proximal member 118, the distal member 120, and the medial member 122. As an example, the protrusions 148 may be formed of a material that may be softer or more elastic than material of the main body 112 so that the engagement member 107 of the proximal portion 103 of the stent graft 102 may be secured to the retaining member 110. The protrusions 148 may be formed of a polymeric material such as a thermoplastic elastomer including a polyether block amide (e.g., Pebax®) or another suitable material, as required. A range of material grades of Pebax® may form the protrusions 148 such as Pebax® 6333 SA 01 MED resin and Pebax® 7033 SA 01 MED or another grade disposed therebetween. The protrusions 148 may have a Shore D Hardness 15s that may range between 53 and 63 and a nominal strain at break that may be greater than 40%. The protrusions 148 and the interstices 150 may increase a coefficient of friction between the retaining member 110 and the proximal end 103 of the stent graft 102 to selectively secure the proximal end 103 of the stent graft to the retaining member 10.

FIG. 6 illustrates the guide member 108 of the delivery system 100 and the stent graft 102 during deployment of the stent graft 102. The stent graft 102 may include the proximal portion 103 and a distal portion 154 that may be inserted to a deployment location 158 (represented by dashed box). As the stent graft 102 is deployed the graft cover 106 may be retracted from the distal portion 154 of the stent graft 102 towards the proximal portion 103 of the stem graft 102. Portions of the stent graft 102 that are uncovered when the graft cover 106 is retracted may change from the radially compressed configuration to the radially deployed configuration so that uncovered portions of the graft wall 109 and the stent ring 105 expand radially to lie against a wall 156 of the blood vessel 104. Under certain conditions, portions of the stent graft 102 may lurch or move forward in an axial direction A away from the guide member 108 and towards and past the deployment location 158. Such unintentional movement of the stent graft 102 may be detrimental to deployment accuracy of the stent graft 102.

The retaining member 110 of the guide member 108 may be configured to engage and secure the engagement member 107 formed by or disposed on the proximal portion 103 of the stent graft 102 to prevent or at least mitigate unintentional axial movement of the stent graft 102. As an example, the engagement member 107 may be formed by a number of radio-opaque markers 152 (RO markers) that may be disposed on an inner or outer periphery of the stent graft 102. The radio-opaque markers 152 may have a substantially spherical shape that may have an outer diameter that may range between 0.03 inches and 0.06 inches. As another example, the radio-opaque markers 152 may not be spherical (e.g., cube, rectangular, pyramid shape) and have a thickness that may range between 0.03 inches and 0.06 inches. Alternatively or additionally, the engagement member 107 may include one or more portions of the stent spring 105 or the graft wall 109.

As an example, the notch 124 collectively formed by the proximal member 118, medial member 122, and the distal member 120 forms a gap G disposed between the medial member 122 and the graft cover 106. The engagement member 107 of the stent graft 102, such as the radio opaque marker 152 may be trapped within the gap G and one or more portions of the proximal member 118, medial member 122, and the distal member 120 may engage and secure the engagement member 107, such as the radio opaque marker 152, so that the stent graft 102 is held in place. The gap G is positioned below the graft cover 106 so that the graft cover 106 may be moved or retracted without dislodging the engagement member 107 from the gap G. As an example, the size of the gap G may be the same or substantially the same as a thickness of the retaining member 107 (e.g., radio opaque marker, stent, etc.). The size or height of the gap G may be formed by a difference between outer diameters of D2 and D1 and D3 so that at least portions of the engagement member 107 including the radio opaque marker 152 are sandwiched between the graft cover 106 and the medial member 122. The height of the gap G may also be sized without increasing the diameter of the delivery system 100 (FIG. 1) beyond the outer diameter D1 of the proximal member 118 to prevent excessive insertion forces.

One or more portions of the retaining member 114 may engage the engagement member 107 so that the engagement member 107 is secured by frictional forces between retaining member 114 and the engagement member 107. Alternatively or additionally, an end face 160 of the proximal member 118 or an end face 162 of the distal member 120 may engage and secure the engagement member 107 (FIG. 7).

In one or more embodiments, the proximal portion 103 of the stem graft 102 may be positioned in a proximal deployment location 159. The proximal deployment location 159 is spaced apart from the distal deployment location 158 and is positioned closer to the handle 116 (FIG. 1) of the delivery system 100. As an example, the proximal deployment location 159 may be defined by an ascending thoracic aorta, an aortic arch, a descending thoracic aorta, or an abdominal aorta, each of which may be reinforced by the main stent graft 126 (FIG. 2). As another example, the proximal deployment location 159 may be defined by an intersection between the main stent graft 126 and the branch stent graft 128 (FIG. 2). The branch stent graft 128 may be inserted within a number of aorta branches including but not limited to the brachiocephalic (BCA), left common carotid (LCC), left subclavian (LSA), a celiac trunk, superior mesenteric, renal, gonadal, inferior mesenteric, and common iliac.

FIG. 7 illustrates a schematic-plan view of a portion of the guide member 108 and the stent graft 102 in the radially deployed configuration. For purposes of clarity, the graft cover 106 and blood vessel 104 are not illustrated. The retaining member 110 of the guide member may be collectively formed by the proximal member 118, the distal member 120, and the medial member 122. In one or more embodiments, the end face 160 of the proximal member 118 and the end face 162 of the distal member 120 may be configured to engage the engagement member 107 such as one or more of the radio-opaque markers 152. As another example, the medial member 122 may be configured to engage the radio-opaque markers 152.

In at least one embodiment, the one or more engagement members 107 may be one or more RO markers 152 or other non-stent item(s) attached to the graft material of a stent graft, such as a branch stent graft 128. As described above, when the branch stent graft 128 is in a compressed state within the delivery system, the RO marker(s) may be located within the gap G between the medial member 122 and the graft cover 106 within the third length L3. The entire RO marker(s) may be located within the length L3. The stent graft may have a proximal most stent, or a stem closest to the handle of the delivery system that is configured to be deployed last as the graft cover 106 is retracted. In at least one embodiment, the proximal most stent may have a length or height (e.g., from peak to trough of a sinusoidal stent) that is larger than the length L3. Stated another way, the length L3 may be smaller than a length/height of the proximal most stent such that the proximal most stent cannot fit completely within length L3 and cannot be trapped completely between proximal member 118 and distal member 120 in the gap G between graft cover 106 and medial member 122. For example, the length L3 may be about 3 mm to about 5 mm (e.g., about 4 mm) while a length/height of the stent may be 6 mm or greater (e.g., 8 mm, 9 mm or greater).

In at least one embodiment, the proximal most stent may extend partially along the medial member 122 within the length L3 and extend at least partially along the distal member 120 within L4 (or beyond). An example of this arrangement may be shown in FIG. 7. A thickness or diameter of the proximal most stent may generally correspond (e.g., be about equal) to a difference in the diameter D1 of proximal member 118 and diameter D3 of distal member 120. Accordingly, the proximal most stent may not be held in place by the graft cover 106 and the guide member 108 (e.g., absent the engagement member 107, the stent would not be retained in the gap G when axial force in the distal direction is applied).

The RO marker(s) 152 may be sized such that they fit completely within length L3 and, therefore, can be trapped completely between proximal member 118 and distal member 120 in the gap G between graft cover 106 and medial member 122. The RO marker(s) 152 may be attached to the graft material of the stent graft at a proximal end of the stent graft (e.g., as shown in FIGS. 6 and 7). As described above, the thickness of the RO marker(s) 152 may correspond to a size of the gap G, such that until the graft cover 106 is retracted proximally past the RO marker, the RO marker, and therefore the proximal end of the stent graft, will be held in place within the gap G along length L3 of the medial member 122. The thickness of the RO marker may therefore be larger than the thickness/diameter of the proximal most stent. In at least one embodiment, the proximal most stent of the stent graft may be allowed to at least partially expand while the stent graft is still retained by the RO marker(s). For example, as defined by the percentage of stent length/height exposed, the stent graft may be at least 50%, 67%, 75%, or 90% expanded while the stent graft is still retained by the RO marker(s). In the partially expanded state, the distal end of the stent (opened first) may be in contact with the vessel wall while the RO marker(s) are still being held in place. In one embodiment, the RO marker(s) may be completely proximal to the proximal most stent (e.g., by at least 1, 2, or 3 mm), which would allow the proximal most stent to be completely expanded prior to release of the RO marker. This may delay the full release of the stent graft until the last possible moment by maintaining control until the very proximal end of the stent graft is uncovered by the retracting graft cover.

Retaining an RO marker or other non-stent item in the gap G instead of a stent may be beneficial for improving accuracy and control of deployment. If a stent is used as the engagement member 107 and the length L3 is long enough to accommodate the entire stent, once the graft cover is retracted past the distal edge of the stent, the stent may start to expand. When the distal portion of the stent expands, it may pull the proximal end of the stent out of the graft cover (and therefore the remaining portion of the stent graft), even if the graft cover has not yet been retracted proximally past the entire stent. In contrast, if the RO marker is still trapped within the gap G, proximal to the distal member 120, even when the proximal most stent begins to expand, the stent graft will still be held to the delivery system and the stent graft cannot “jump” or move distally under the force of the expanding stent.

While embodiments have been described herein with reference to stent grafts and endovascular treatment of aneurysms, the delivery systems may also be applicable to other catheter-based medical devices. For example, instead of endovascular repair of aortic aneurysms, the disclosed delivery systems may be used for transcatheter heart valve devices, such as those for the aortic valve (e.g., TAVR) or for the mitral or tricuspid valves. In such examples, the engagement member may be any suitable portion of the device, such as a stent, radio opaque marker, cage, leaflet retention feature, skirt/wrap material, or others.

While exemplary embodiments are described above, it is not intended that these embodiments describe all possible forms encompassed by the claims. The words used in the specification are words of description rather than limitation, and it is understood that various changes can be made without departing from the spirit and scope of the disclosure.

As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An endovascular delivery system comprising:

a stent graft including a first end and a second end, the first end including an engagement member, the stent graft configured to change between a radially compressed configuration and a radially deployed configuration, the stent graft includes stent rings and a graft wall;

a graft cover radially covering at least a portion of the stent graft and configured to retract to uncover the stent graft so that the stent graft changes from the radially compressed configuration to the radially deployed configuration; and a guide member configured to carry the stent graft and the graft cover, the first end of the stent graft is arranged closer to a proximal end of the guide member than the second end of the stent graft, the guide member securing the first end of the stent graft in a first position where the engagement member is held between the graft cover and the guide member to hold the first end of the stent graft in the first position as the graft cover is retracted to deploy the stent graft, the first end of the stent graft includes a proximal most end contacted by the graft cover in the first position, the guide member includes a proximal end portion and a distal end portion, the distal end portion includes a proximal member, a distal member, and a medial member extending between the proximal member and the distal member, and the engagement member contacts the medial member and is spaced apart from the graft cover by the stent graft including the stent rings and the graft wall, the stent graft is radially situated between the graft cover and the engagement member.

2. The delivery system of claim 1, wherein the guide member includes a main body defining a first hardness and the distal end portion defines a second hardness, the distal end portion forms the engagement member and the second hardness is less than the first hardness so that the medial member is configured to receive the engagement member of the stent graft.

3. The delivery system of claim 2, wherein the distal end portion includes a number of protrusions radially extending from an outer periphery of the distal end portion.

4. The delivery system of claim 3, wherein the distal end portion includes a number of interstices disposed between each of the number of protrusions.

5. The delivery system of claim 1, wherein the guide member includes an elongated body, and an outer periphery of a distal end portion of the elongated body includes a number of surface discontinuities collectively configured to engage the engagement member of the stent graft.

6. The delivery system of claim 5, wherein the number of surface discontinuities are formed by a number of knurls.

7. An endovascular delivery system comprising:

a stent graft including a first end and a second end, the first end including an engagement member, the stent graft configured to change between a radially compressed configuration and a radially deployed configuration, the stent graft includes stent rings and a graft wall;

a graft cover radially covering at least a portion of the stent graft and configured to retract to uncover the stent graft so that the stent graft changes from the radially compressed configuration to the radially deployed configuration; and a guide member configured to carry the stent graft and the graft cover, the first end of the stent graft is arranged closer to a proximal end of the guide member than the second end of the stent graft, the guide member securing the first end of the stent graft in a first position where the engagement member is held between the graft cover and the guide member to hold the first end of the stent graft in the first position as the graft cover is retracted to deploy the stent graft, the first end of the stent graft includes a proximal most end contacted by the graft cover in the first position, the guide member includes a proximal end portion and a distal end portion, the distal end portion includes a proximal member, a distal member, and a medial member extending between the proximal member and the distal member, the distal member has a distal member diameter less than a proximal member diameter of the proximal member, and the engagement member contacts the medial member and is spaced apart from the graft cover by the stent graft including the stent rings and the graft wall, the stent graft is radially situated between the graft cover and the engagement member.

8. The delivery system of claim 7, wherein at least one of the proximal member and the distal member forms edge portions.

9. The delivery system of claim 7, wherein the guide member includes a main body defining a first hardness and the distal end portion defines a second hardness, the distal end portion forms the engagement member and the second hardness is less than the first hardness so that the medial member is configured to receive the engagement member of the stent graft.

10. The delivery system of claim 9, wherein the distal end portion includes a number of protrusions radially extending from an outer periphery of the distal end portion.

11. The delivery system of claim 10, wherein the distal end portion includes a number of interstices disposed between each of the number of protrusions.

12. The delivery system of claim 7, wherein the guide member includes an elongated body, and an outer periphery of a distal end portion of the elongated body includes a number of surface discontinuities collectively configured to engage the engagement member of the stent graft.

13. The delivery system of claim 12, wherein the number of surface discontinuities are formed by a number of knurls.

14. An endovascular delivery system comprising:

a stent graft including a first end and a second end, the first end including an engagement member, the stent graft configured to change between a radially compressed configuration and a radially deployed configuration, the stent graft includes stent rings and a graft wall;

a graft cover radially covering at least a portion of the stent graft and configured to retract to uncover the stent graft so that the stent graft changes from the radially compressed configuration to the radially deployed configuration; and a guide member configured to carry the stent graft and the graft cover, the first end of the stent graft is arranged closer to a proximal end of the guide member than the second end of the stent graft, the guide member securing the first end of the stent graft in a first position where the engagement member is held between the graft cover and the guide member to hold the first end of the stent graft in the first position as the graft cover is retracted to deploy the stent graft, the first end of the stent graft includes a proximal most end contacted by the graft cover in the first position, the guide member includes a proximal end portion and a distal end portion, the distal end portion includes a proximal member, a distal member, and a medial member extending between the proximal member and the distal member, the engagement member contacts the medial member and is spaced apart from the graft cover by the stent graft including the stent rings and the graft wall, the stent graft is radially situated between the graft cover and the engagement member, the stent rings having a first thickness, the engagement member has a second thickness, and the second thickness is greater than the first thickness.

15. The delivery system of claim 14, wherein the distal member has a distal member diameter less than a proximal member diameter of the proximal member, and at least one of the proximal member and the distal member forms edge portions.

16. The delivery system of claim 14, wherein the guide member includes a main body defining a first hardness and the distal end portion defines a second hardness, the distal end portion forms the engagement member and the second hardness is less than the first hardness so that the medial member is configured to receive the engagement member of the stent graft.

17. The delivery system of claim 16, wherein the distal end portion includes a number of protrusions radially extending from an outer periphery of the distal end portion.

18. The delivery system of claim 17, wherein the distal end portion includes a number of interstices disposed between each of the number of protrusions.

19. The delivery system of claim 14, wherein the guide member includes an elongated body, and an outer periphery of a distal end portion of the elongated body includes a number of surface discontinuities collectively configured to engage the engagement member of the stent graft.

20. The delivery system of claim 19, wherein the number of surface discontinuities are formed by a number of knurls.

* * * * *